US007778387B2

(12) United States Patent
Koehler et al.

(10) Patent No.: US 7,778,387 B2
(45) Date of Patent: Aug. 17, 2010

(54) RECONSTRUCTION METHOD FOR HELICAL CONE-BEAM CT

(75) Inventors: Thomas Koehler, Norderstedt (DE); Claas Bontus, Hamburg (DE); Peter Koken, Hamburg (DE)

(73) Assignee: Koninklijke Philips Electronics N. V., Eindhoven (NL)

( * ) Notice: Subject to any disclaimer, the term of this patent is extended or adjusted under 35 U.S.C. 154(b) by 289 days.

(21) Appl. No.: 11/913,821

(22) PCT Filed: May 3, 2006

(86) PCT No.: PCT/IB2006/051388

§ 371 (c)(1),
(2), (4) Date: Nov. 7, 2007

(87) PCT Pub. No.: WO2006/120611

PCT Pub. Date: Nov. 16, 2006

(65) Prior Publication Data
US 2009/0268863 A1 Oct. 29, 2009

(30) Foreign Application Priority Data
May 13, 2005 (EP) ................................. 05104025

(51) Int. Cl.
*A61B 6/00* (2006.01)
(52) U.S. Cl. ................................. 378/19; 378/4; 378/15
(58) Field of Classification Search ..................... 378/4, 378/15
See application file for complete search history.

(56) References Cited

U.S. PATENT DOCUMENTS 6,078,638 A * 6/2000 Sauer et al. .................... 378/4

6,269,141 B1 * 7/2001 Proksa et al. ................. 378/19
2003/0142778 A1 * 7/2003 Proksa ........................... 378/4

(Continued)

FOREIGN PATENT DOCUMENTS

DE         10252661 A1     5/2004

(Continued)

OTHER PUBLICATIONS

Katsevich, 3PI algorithms for helical computer tomography, Science Direct, Advances in Applied Mathematics, 36, 2006, pp. 213-250.*

(Continued)

*Primary Examiner*—Edward J Glick
*Assistant Examiner*—Alexander H Taningco (57) ABSTRACT

The invention relates to a method and a system for the reconstruction of an object function (f(x)) based on projections acquired during the motion of a radiation source on a helical trajectory (17). The method is particularly suited for an n-PI+ acquisition which by definition completely comprises an n-PI and additionally some overscan data from the (n+2)-PI window. According to the method, two sets ($\Sigma \leq m$, $\Sigma > m$) of filtered projections are generated from the measuring values and separately back-projected to yield two absorption functions. The first absorption function ($f^{lf}(x)$) is based on contributions of Radon-planes with at most m intersections with the source trajectory (17), while the second absorption function ($f^{hf}(x)$) is based on Radon-planes with more than m intersections with the source trajectory (17). The two absorption functions are added to yield the final absorption function (f(x)) of an object in the examination zone. In an approximative version of the method, the sets ($\Sigma \leq m$, $\Sigma > m$) of filtered projections are first added and then back-projected.

17 Claims, 8 Drawing Sheets

U.S. PATENT DOCUMENTS

2004/0125910 A1*   7/2004   Katsevich .................... 378/15
2006/0039525 A1    2/2006   Bontus et al.
2006/0233294 A1*  10/2006   Bontus et al. ................. 378/4
2008/0013676 A1*   1/2008   Bontus et al. ................. 378/17

OTHER PUBLICATIONS

Bontus et al., CEnPIT: Helical cardiac CT reconstruction, Med Phys, 33, 8, Aug. 2006, pp. 2792-2799.*

Bontus, C., et al.; EnPiT: Filtered Back-Projection Algorithm for Helical CT Using an n-Pi Acquisition; 2005; IEEE Trans. on Medical Imaging; 24(8)977-986.

Bontus, C., et al.; EnPiT: A reconstruction algorithm for helical CT; 2004; IEEE Nuclear Science Symposium Conference; pp. 3027-3030.

Bontus, C., et al.; A quasiexact reconstruction algorithm for helical CT using a 3-Pi acquisition; 2003; Med. Phys.; 30 (9)2493-2502.

Katsevich, A.; Analysis of an exact inversion algorithm for spiral cone-beam CT; 2002; Phys. Med. Biol.; 47:2583-2597.

Kohler, T., et al.; The Radon-split Method for Helical Cone-Beam CT and Its Application to Nongated Reconstruction; 2006; IEEE Trans. on Medical Imaging; 25(7)882-897.

Kohler, T., et al.; A New Approach to Handle Redundant Data in Helical Cone-Beam CT; 2005; 8th Int'l. Mtg. on Fully Three-Dimensional Image Reconstruction in Radiology and Nuclear Medicine; pp. 19-22. http://www.fully3d.org/2005/3D05Proceedings.pdf.

* cited by examiner

RECONSTRUCTION METHOD FOR HELICAL CONE-BEAM CT

The invention relates to a computed tomography method in which an examination zone is irradiated along a helical trajectory by a conical X-ray beam. Moreover, the invention relates to a computer tomograph as well as to a computer program and a record carrier for controlling the computer tomograph.

In many computed tomography (CT) methods of the kind set forth, the absorption function of an object in the examination zone is approximately reconstructed from the measuring values acquired by a detector unit. Exact and quasi-exact reconstruction methods for helical CT are currently known only for the n-PI acquisition, wherein, for an odd number n, the used detector area is bounded by the projection of (n+1) turns of the helical source trajectory onto the detector area (cf. DE 102 52 661 A1 and C. Bontus, T. Koehler, R. Proksa: "A quasiexact reconstruction algorithm for helical CT using a 3-Pi acquisition," Med. Phys., vol. 30, no. 9, pp. 2493-2502 (2003), which are incorporated into the present application by reference). These methods provide excellent image quality for static objects, but due to the restriction to the n-PI acquisition, they are quite sensitive to motion artifacts. Approximative reconstruction methods, on the other hand, are not restricted to n-PI acquisitions, but suffer from artifacts in the reconstructed images which increase with growing cone angle in axial direction.

Based on this situation it was an object of the present invention to provide means that allow a fast, high-quality reconstruction of absorption functions without being restricted to certain acquisition windows.

This object is achieved by a computed tomography reconstruction method, a computer tomograph, a computer program, and a record carrier.

According to its first aspect, the invention is related to a computed tomography reconstruction method whereby the absorption function (f(x)) of object points (x) in the examination zone (13) is based on two non-empty sets ($\Sigma_{\leq m}$, $\Sigma_{>m}$) of filtered projections, wherein for a predetermined odd number m≤n:
  the first set ($\Sigma_{\leq m}$) of filtered projections yields, when back-projected, a first absorption function ($f^{lf}(x)$) that contains only contributions of Radon-planes with at most m intersections with the source trajectory (17);
  the second set ($\Sigma_{>m}$) of filtered projections yields, when back-projected, a second absorption function ($f^{hf}(x)$) that contains only contributions of Radon-planes with more than m intersections with the source trajectory (17);
  at least one of the sets ($\Sigma_{\leq m}$, $\Sigma_{>m}$) of filtered projections contains contributions from measuring values outside the n-PI window.

A method of the aforementioned kind has the advantage to exploit available measuring values beyond the n-PI window. In contrast to known exact or quasi-exact methods, there is no restriction to exactly an n-PI window which would lead to a loss of information and a waste of dose. The advantage of the method is achieved by a (conceptually) split reconstruction for Radon-planes with firstly at most m and secondly with more than m intersections with the source trajectory. Based on this approach, different concrete algorithms of the filtered back-projection type can be provided for the reconstruction of the absorption function.

Preferred realizations with respect to embodiments will be discussed in more detail below.

The term "helical" in the following shall be understood in a general sense as a spiral or threadlike shape without being restricted to mathematically exact helices, though the latter will commonly describe the relative movement of radiation source and object. Moreover, it should be noted that the two sets of filtered projections need not necessarily be generated as intermediate results; instead, the method shall also comprise reconstruction algorithms that achieve the same final result without explicitly generating these sets.

The predetermined odd number m that is used to characterize the two sets of filtered projections is preferably equal to n, i.e. the maximal PI window size that is completely covered by the acquisition. In this case the first set of filtered projections reaches a maximal size, which is advantageous if exact or quasi-exact reconstruction algorithms are applied on this set.

Preferably the second set of filtered projections yields, when back-projected, an absorption function $f^{hf}(x)$ that contains contributions from almost all Radon-planes with more than m intersections with the source trajectory. In the following, the term "almost all" means, in a strict mathematical sense, that the missing Radon-planes occupy a volume of measure zero. The use of almost all Radon-planes with more than m intersections leads to an optimal exploitation of the overscan data.

In a first basic variant of reconstruction algorithms according to the invention, the first absorption function $f^{lf}(x)$ of object points x in the examination zone is reconstructed from the first set of filtered projections, and the second absorption function $f^{hf}(x)$ of object points x in the examination zone is reconstructed from the second set of filtered projections, wherein said first and second absorption functions are then superposed to yield the final absorption function f(x) of object points x in the examination zone.

According to a second basic variant of the reconstruction algorithm, the final absorption function f(x) of object points x in the examination zone is reconstructed based on a third set of filtered projections, wherein said third set corresponds to the point-by-point or pixel-wise sum of the first and the second set of filtered projections. As the reconstruction typically involves back-projections, this second variant is computationally less expensive because only one back-projection (based on the third set) is necessary.

In a particular further embodiment of the invention, the computed tomography method comprises the following steps:
  the partial derivative $D_f'$ of measuring values, which are generated by parallel rays emanating from different radiation source positions, is determined with respect to the angular position s of the radiation source;
  the first and the second set of filtered projections comprise for each measuring value a first filtered value $P^{lf}(s,x)$ and a second filtered value $P^{hf}(s,x)$, respectively, wherein:
    each first and second filtered value $P^{lf}(s,x)$, $P^{hf}(s,x)$ corresponds to a weighted sum, with filter factors $\mu_\nu^{lf}$, $\mu_\nu^{hf}$, of first and second intermediate filtered values $P_\nu^{lf}(s,x)$ and $P_\nu^{hf}(s,x)$, respectively, and
    each of said intermediate filtered values $P_\nu^{lf}(s,x)$, $P_\nu^{hf}(s,x)$ is the result of filtering the derived measuring values along an associated filtering line with a K-filter;
  the absorption function f(x) of object points x in the examination zone is reconstructed by weighted back-projection of the first and second filtered values $P^{lf}(s,x)$, $P^{hf}(s,x)$.

The aforementioned steps characterize reconstruction algorithms of the so-called EnPiT-type (cf. C. Bontus, T. Koehler, R. Proksa: "EnPiT: A reconstruction algorithm for helical CT", Proceedings of the IEEE Medical Imaging Conference, Rome, Italy, (2004); C. Bontus, T. Koehler, R. Proksa: "EnPiT: Filtered back-projection for helical CT using an n-Pi acquisition", IEEE Trans. Med. Imag., (accepted for publication in 2005); both articles are incorporated into the present application by reference). These algorithms yield, in case of properly defined filter lines, exact or quasi-exact results with well investigated properties.

The K-filter that is mentioned in the previous embodiment preferably corresponds to a convolution with (1/sin γ), wherein the angle γ will be explained in more detail in the description of the Figures.

In the EnPiT-type algorithms mentioned above, the proper definition of filter lines is of crucial significance. Sets of filter lines, associated filter factors µ, and weighting factors for back-projection that allow a discrimination between the contribution of Radon-planes with different numbers of intersections with the source trajectory are defined in claims 8 to 13 and illustrated in the Figures.

According to a further development of the method, the elements of one of the two sets of filtered projections are selected according to a cardiac gating scheme. In cardiac gating, projections of the beating heart are admitted or rejected from processing according to the heart phase during which they were generated, wherein the heart phase is typically determined from ECG signals. The gating is preferably done on projections of the second set of filtered projections because they correspond to Radon-planes with a higher number of intersections with the helix and thus relate to data which have been measured with high redundancy.

A computer tomograph for carrying out the computed tomography reconstruction method is disclosed. Also disclosed is a computer program for controlling such a computer tomograph, a record carrier, for example a floppy disk, a hard disk, or a compact disc (CD), on which such a computer program is stored.

These and other aspects of the invention will be apparent from and elucidated with reference to the embodiment(s) described hereinafter.

In the following the invention is described by way of example with the help of the accompanying drawings in which.

Figure 1:
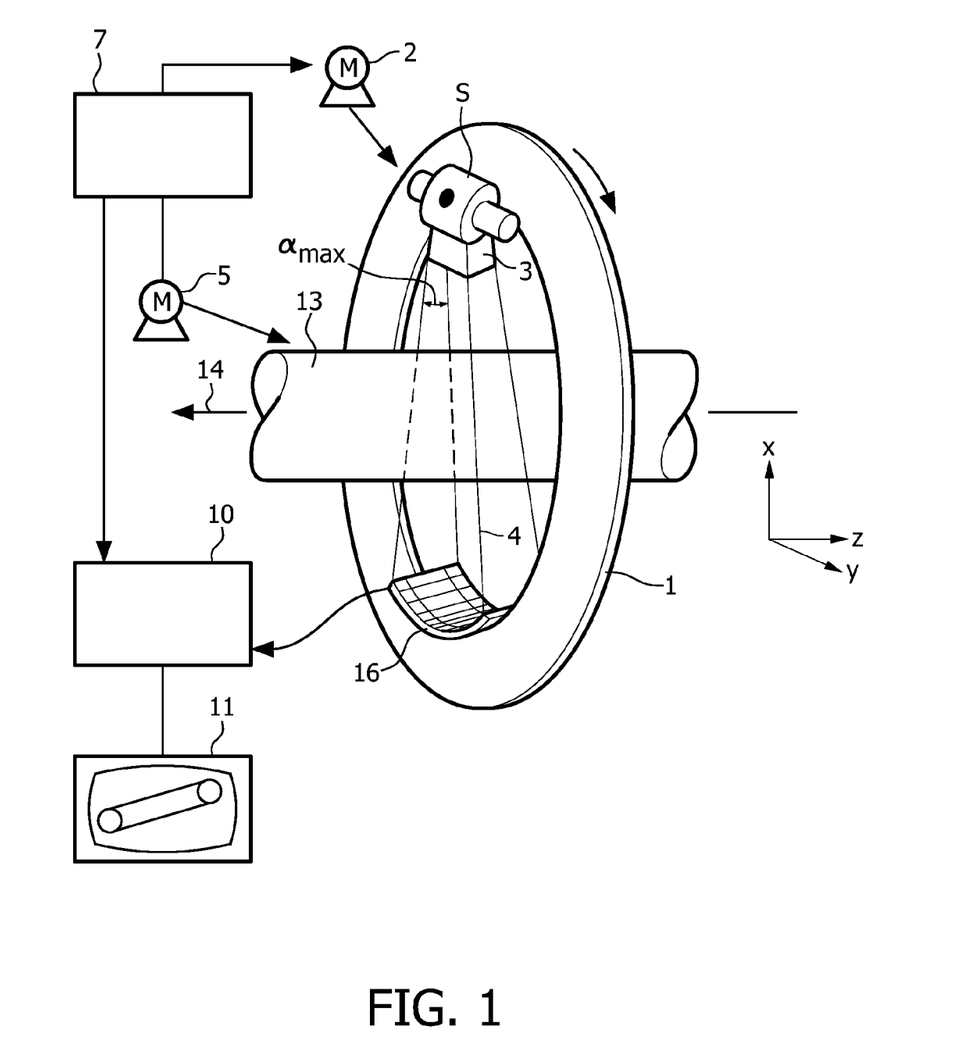
FIG. 1 shows a computer tomograph which is adapted for carrying out the method in accordance with the invention.

The computer tomograph shown in FIG. 1 comprises a gantry 1 which is capable of rotation about an axis of rotation 14 which extends parallel to the z direction of the co-ordinate system shown in FIG. 1. To this end, the gantry 1 is driven by a motor 2 at a preferably constant, but adjustable angular speed. A radiation source S, for example, an X-ray source, is mounted on the gantry 1. The radiation source is provided with a collimator arrangement 3 which forms a conical radiation beam 4 from the radiation generated by the radiation source S, that is, a radiation beam which has a finite dimension other than zero in the z direction as well as in a direction perpendicular thereto (that is, in a plane perpendicular to the axis of rotation).

The radiation beam 4 traverses a cylindrical examination zone 13 in which an object, for example, a patient on a patient table (both not shown) or also a technical object may be situated. After having traversed the examination zone 13, the radiation beam 4 is incident on a detector unit 16 which is attached to the gantry 1 and comprises a detector surface which comprises a plurality of detector elements arranged in rows and columns in the form of a matrix in the present embodiment. The detector columns extend parallel to the axis of rotation 14. The detector rows are situated in planes which extend perpendicularly to the axis of rotation, that is, preferably on an arc of a circle around the radiation source S (focus centered detector area). However, they may also have a different shape, for example, an arc of a circle around the axis of rotation 14 or be rectilinear. Generally speaking, the detector rows comprise more detector elements (for example, 1000) than the detector columns (for example, 16). Each detector element struck by the radiation beam 4 produces a measuring value for a ray of the radiation beam 4 in each position of the radiation source.

The angle of aperture of the radiation beam 4, denoted by the reference $\alpha_{max}$, determines the diameter of the object cylinder within which the object to be examined is situated during the acquisition of the measuring values. The angle of aperture is defined as the angle enclosed by a ray situated at the edge of the radiation beam 4 in a plane perpendicular to the axis of rotation with respect to a plane defined by the radiation source S and the axis of rotation 14. The examination zone 13, or the object or the patient table, can be displaced parallel to the axis of rotation 14 or to the z axis by means of a motor 5. As an equivalent, however, the gantry could also be displaced in this direction.

When a technical object is concerned instead of a patient, the object can be rotated during an examination while the radiation source S and the detector unit 16 remain stationary.

Figure 4:
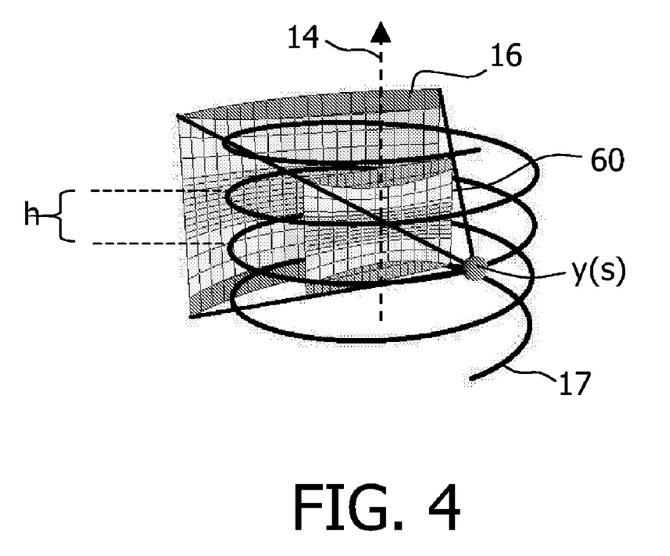
FIG. 4 shows a perspective view of the helical trajectory of a radiation source in a 3-PI acquisition together with a focus centered and a virtual planar detector area, respectively.
Figure 5:
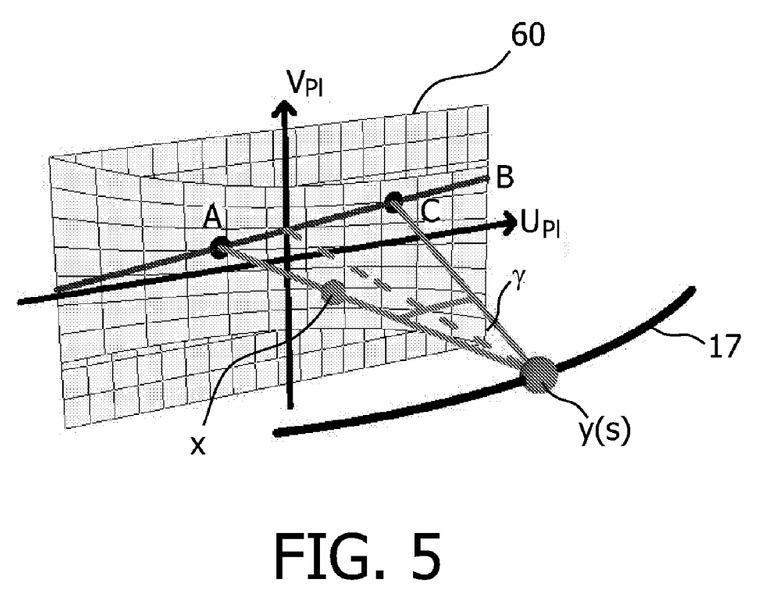
FIG. 5 illustrates in a perspective view of the source position and the virtual planar detector area the definition of the angle γ.

When the motors 2 and 5 operate simultaneously, the radiation source S and the detector unit 16 describe a helical trajectory relative to the examination zone 13. However, when the motor 5 for the displacement in the direction of the axis of rotation 14 is stationary and the motor 2 rotates the gantry, a circular trajectory is obtained for the radiation source and the detector unit 16 relative to the examination zone 13. Hereinafter, only the helical trajectory will be considered. Such a helical trajectory 17 (FIGS. 4, 5) can be described by the equation $$y(s)=(R \cos s, R \sin s, sh/2\pi)^T \qquad (1)$$

with R being the radius of the helix 17, s being the angular position of the radiation source on the helix, and h being the pitch, i.e. the distance between two neighbouring turns of the helix 17 (cf. FIG. 4).

The measuring values acquired by the detector unit 16 are applied to an image processing computer 10 which is connected to the detector unit 16, for example, via a wireless data transmission (not shown). The image processing computer 10 reconstructs the absorption distribution in the examination zone 13 and reproduces it, for example, on a monitor 11. The two motors 2 and 5, the image processing computer 10, the radiation source S and the transfer of the measuring values from the detector unit 16 to the image processing computer 10 are controlled by a control unit 7.

In other embodiments the acquired measuring values can first be applied to one or more reconstruction computers for reconstruction, said computers applying the reconstructed data to the image processing computer, for example, via an optical fiber cable.

Figure 2:
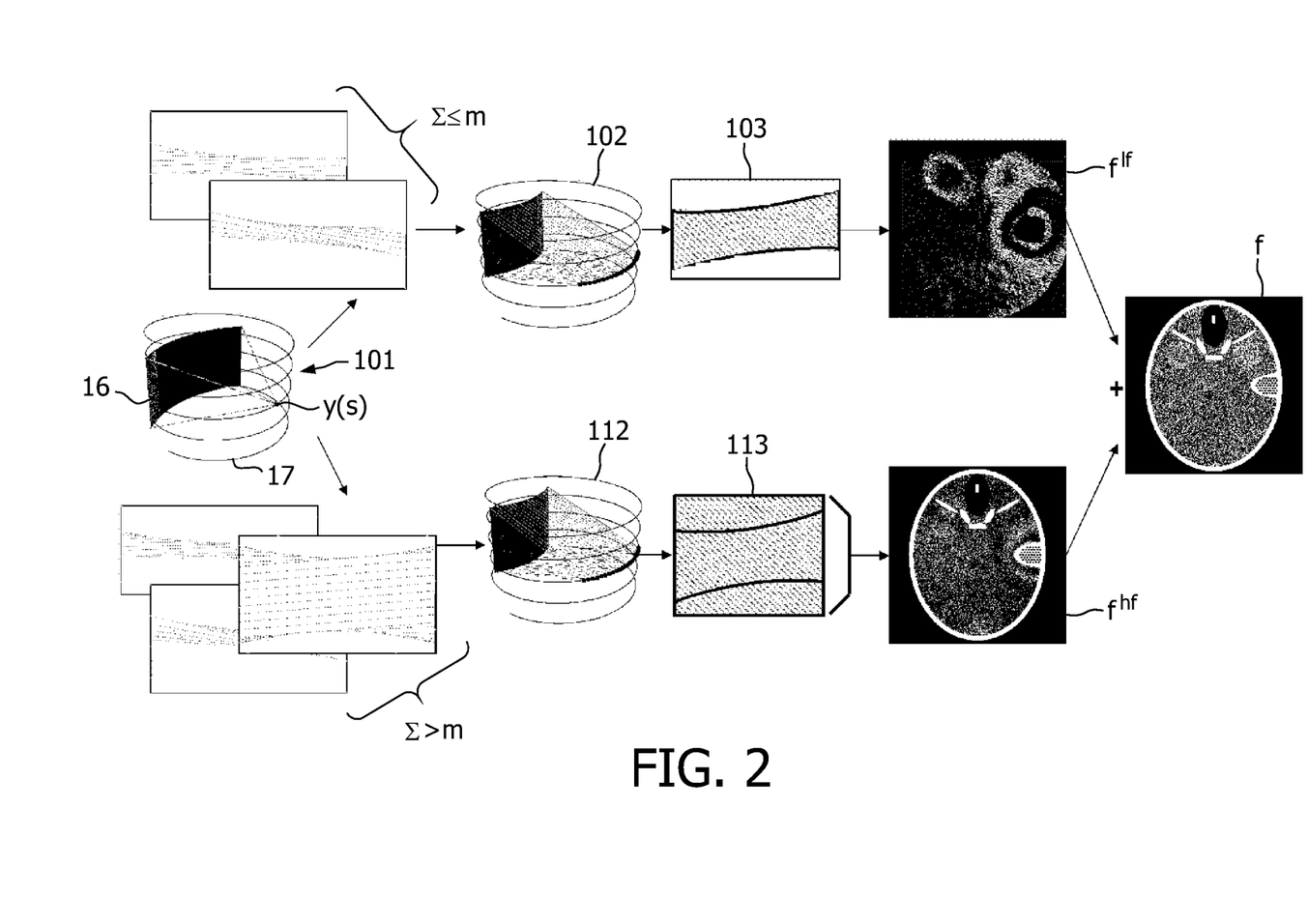
FIG. 2 illustrates a first variant of carrying out the method in accordance with the invention, wherein a first and a second set of projections are back-projected and the resulting images are added.

FIG. 2 illustrates a first basic variant of a measuring and reconstruction method that can be executed by means of the computer tomograph shown in FIG. 1.

The data acquisition process is symbolized at reference number 101 in FIG. 2. It starts with the initialization of the system, after which the gantry rotates at an angular speed which is constant in the present embodiment. However, it may also vary, for example, in dependence on the time or on the radiation source position. In the next step, the examination zone (or the object or the patient table) is displaced parallel to the axis of rotation and the radiation of the radiation source S is switched on, so that the detector unit 16 can detect the radiation from a plurality of source positions y(s). Thus, a series of two-dimensional projections of the examination zone is produced which form the raw data from which the absorption function of the object has to be reconstructed.

In the next step of the algorithm, a first and a second set $\Sigma_{\leq m}$ and $\Sigma_{>m}$ of filtered projections are calculated from the aforementioned raw projections for a predetermined odd number m. A "filtered projection" is a two-dimensional array of data in which each element or position corresponds bijectively to an element/position on the detector area of the raw projections and in which the value of each element/position is calculated from said raw data. Examples of filtered projections will be described in more detail below.

In the next steps 102, 112 of FIG. 2, the first and second sets $\Sigma_{\leq m}$, $\Sigma_{>m}$ of filtered projections are re-binned into a parallel geometry. These steps are optional and primarily a technical measure to increase computational efficiency and accuracy without influencing the principal outcome of the method. For a more detailed description of the re-binning step, reference is made to the DE 102 52 661 A1.

In the next steps 103, 113 of the algorithm, the filtered (and optionally re-binned) projections are back-projected, yielding a first absorption function $f^{lf}(x)$ and a second absorption function $f^{hf}(x)$, respectively. As will be explained in more detail below, the back-projection is done with an aperture (or angular) weighting, wherein a constant non-zero weight is applied inside the n-PI window in step 103, while all data are used in step 113.

In the final step, the two absorption functions $f^{lf}(x)$ and $f^{hf}(x)$ are added to yield the final absorption function f(x) or tomographic image of the object in the examination zone.

The difference between the upper and the lower reconstruction path in FIG. 2 lies in the different use of Radon-planes. Given an object function f(x), the Radon transform Rf of this function at $\rho\omega$ is defined as $$Rf(\rho, \omega) = \int_{-\infty}^{\infty} d^3 x f(x) \delta(\rho - \omega \cdot x) \quad (2)$$

i.e., $Rf(\rho, \omega)$ is a plane integral through f(x), $\omega$ the normal vector of this "Radon-"plane, and $\rho$ the shortest distance of the Radon-plane to the origin. The inverse Radon transform can be written as $$f(x) = \frac{-1}{8\pi^2} \int d\Omega R'' f(\omega \cdot x, x), \quad (3)$$

wherein the integration runs over the whole unit sphere with $\omega = (\cos\phi \sin\theta, \sin\phi \sin\theta, \cos\theta)$ and with $R'' f(\rho, \omega)$ being the Radon transform of f(x) differentiated twice with respect to $\rho$.

The first set $\Sigma_{\leq m}$ of filtered projections in the upper path of FIG. 2 is now designed in such a way that the object function $f^{lf}(x)$ reconstructed therefrom contains only contributions of Radon-planes with at most m intersections with the helical trajectory 17 of the radiation source. With other words, the first function $f^{lf}(x)$ corresponds to the integral $$f^{lf}(x) \propto \frac{-1}{8\pi^2} \int_{K\_lf} d\Omega R'' f(\omega \cdot x, x) \tau_{lf}(\omega), \quad (4)$$

wherein K_lf contains only (but not necessarily all) normal vectors $\omega$ of Radon-planes with at most m intersections with the source trajectory 17, and wherein $\tau_{lf}(\omega)$ is a factor that weights the contribution of each Radon-plane with normal vector $\omega$.

In a similar way, the second set $\Sigma_{>m}$ of filtered projections is designed in such a way that the resulting absorption function $f^{hf}(x)$ contains only (but not necessarily all) contributions of Radon-planes with more than m intersections with the source trajectory 17. With other words, the second function $f^{hf}(x)$ corresponds to the integral $$f^{hf}(x) \propto \frac{1}{8\pi^2} \int_{K\_hf} d\Omega R'' f(\omega \cdot x, x) \tau_{hf}(\omega), \quad (5)$$

wherein K_hf contains only (but not necessarily all) normal vectors $\omega$ of Radon-planes with more than m intersections with the source trajectory 17, and wherein $\tau_{hf}(\omega)$ is a factor that weights the contribution of each Radon-plane with normal vector $\omega$. The additional weights $\tau_{lf}(\omega)$, $\tau_{hf}(\omega)$ are ideally identical to 1 for all $\omega$, meaning that the two images would add up exactly to the object function f. However, exactness may sometimes be sacrificed in order to use all available data ($\tau_{hf}(\omega)$ will for example not be identical to 1 everywhere in the algorithm explained below).

It can be shown that Radon-planes with a small number of intersections with the helix 17 (running more perpendicular to the rotation axis) determine the low-frequency (lf) components of the absorption function, while Radon-planes with a higher number of intersections (running more parallel to the rotation axis) determine the high-frequency (hf) components. Therefore, the first and second function $f^{lf}(x)$ and $f^{hf}(x)$ comprise primarily low-frequency and high-frequency components, respectively, and have been indexed accordingly.

An advantage of the separation of contributions from Radon-planes with different numbers of intersections with the helix 17 is that it is possible to use (quasi-)exact reconstruction algorithms on the first set $\Sigma_{\leq m}$ of filtered projections, while the second set $\Sigma_{>m}$ of filtered projections takes into account all measuring values available on the whole detector area. Thus no information is lost and the radiation dose is optimally used.

Figure 3:
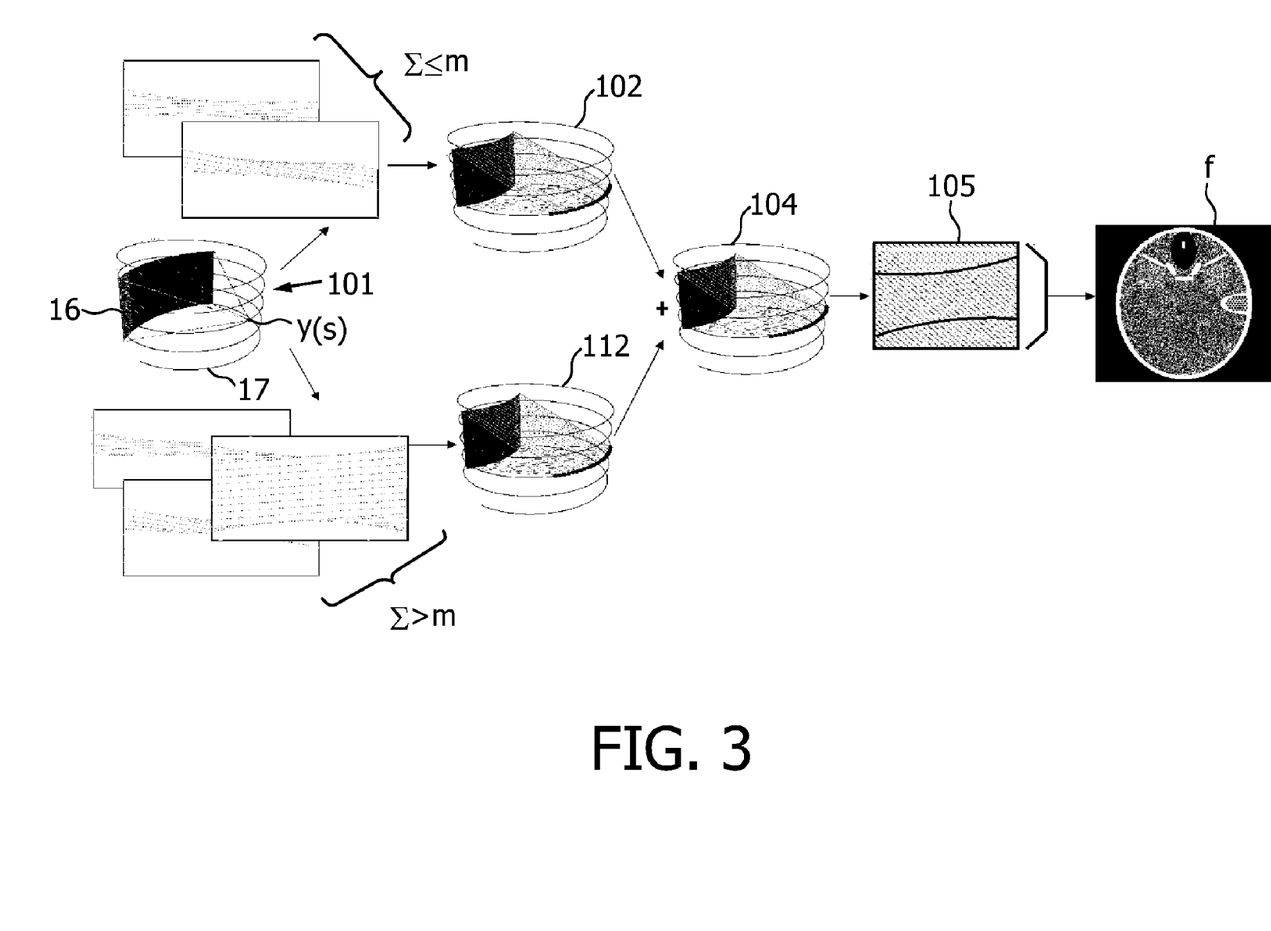
FIG. 3 illustrates a second variant of carrying out the method in accordance with the invention, wherein a first and a second set of projections are first added and then back-projected together.

FIG. 3 shows a second basic variant of the algorithm according to the present invention. As in FIG. 2, two sets $\Sigma_{\leq m}$, $\Sigma_{>m}$ of filtered projections are generated from measuring values and re-binned into parallel geometry, wherein the first set $\Sigma_{\leq m}$ and the second set $\Sigma_{>m}$ contain only contributions of Radon-planes with at most m intersections and more than m intersections with the source trajectory 17, respectively, in the sense defined above.

In difference to FIG. 2, the filtered projections of sets $\Sigma_{\leq m}$, $\Sigma_{>m}$ are not back-projected separately but added point-by-point in step 104. The added data are then back-projected in step 105 with an aperture weighting and a normalization over n-PI partners, yielding the object function f(x). Investigation show that this object function f(x) has, in spite of the applied approximations, a very good image quality. An advantage of the method shown in FIG. 3 is that only one step of back-projection is necessary.

A preferred way for the reconstruction based on a first set $\Sigma_{\leq m}$ and a second set $\Sigma_{>m}$ of filtered projections will be explained in more detail below, wherein the described approach makes use of quasi-exact reconstruction methods for the n-PI acquisition that have been developed in recent years based on an initial work of Alexander Katsevich (cf. A. Katsevich, "Analysis of an exact inversion algorithm for spiral conebeam CT," Phys. Med. Biol. 47, 2583-2597 (2002), and the literature cited above). The absorption function (f(x)) of object points (x) in the examination zone 13 is reconstructed based on two non-empty sets ($\Sigma_{\leq m}, \Sigma_{>m}$) of filtered projections for a predetermined odd number m≦n.

FIG. 4 shows as an example a 3-PI acquisition geometry. In this geometry, the pitch height h is chosen such that, from each position y(s) of the radiation source, at least four neighboring windings of the helical source trajectory 17 are projected onto the detector area 16. In the general case of an odd number n≧3, (n+1) turns of the source trajectory 17 are projected onto the detector area. This situation is called n-PI acquisition and n-PI relative motion.

FIG. 4 further shows a virtual planar detector area 60 which comprises the axis 14 of rotation and which has a normal intersecting the corresponding source position y(s). A coordinate system ($u_{PI}$, $v_{PI}$) is fixed at the center of this detector 60 (cf. FIG. 5).

The known quasi-exact reconstruction methods (cf. citations above) share the feature that the back-projection interval is bounded by PI- or n-PI-lines. In other words, the first and last ray used for reconstruction of an object point are diametrically opposed to each other. There are two major shortcomings of this feature: First, the detector area is not used completely, because the typical detector is cylindrical in shape. Second, this restriction makes the algorithm sensitive to motion artifacts.

In the following, an approximate method to incorporate an arbitrary amount of redundant data will be presented. In order to distinguish it from the aforementioned exact methods, which use no or a fixed amount of redundant data, the additionally used redundant data will be denoted as "overscan". The associated acquisition geometry will be called n-PI+ acquisition, in that there are sufficient data for an exact n-PI reconstruction but not enough data for a (n+2)-PI reconstruction. The symbol + indicates that there are some additional overscan data that shall be used. Measuring values in an n-PI+ window which are dependent on the intensity in the radiation beam on the other side of the examination zone are acquired by means of the detector unit 16 during the helical relative motion, wherein n is an odd number and wherein said n-PI+ window by definition comprises an n-PI but not an (n+2)-PI window.

Reconstruction algorithms of the Katsevich type can generally be separated into three steps: 1. Differentiation, 2. Filtering, 3. Back-projection. These operations are performed on the measuring values or raw data generated during the data acquisition step. For each position y(s) of the radiation source, the measured data correspond to line integrals. Introducing the unit vector 8, the projection data are given by $$D_f(y(s), \theta) = \int_{-\infty}^{\infty} dl f(y + l\theta). \tag{6}$$

In order to handle the overscan data of an n-PI+ acquisition, a first and a second (or low-frequency and high-frequency, respectively) image $f^{lf}(x)$ and $f^{hf}(x)$ are generated separately and then summed to yield the object function f(x). This approach corresponds to the variant illustrated in FIG. 2, but the following explanations can readily be transferred to the situation of FIG. 3, too. Both images, $f^{lf}(x)$ and $f^{hf}(x)$, are generated by the back-projection formula $$f^{xf}(x) = \frac{(-1)}{2\pi^2} \frac{1}{n} \int_{IBP(x)} w^{xf}(x, s) \frac{ds}{|x - y(s)|} \sum_{v=1}^{N_v^{xf}} \mu_v^{xf} \int_{-\pi}^{\pi} \frac{d\gamma}{\sin\gamma} D'_f \tag{7}$$

$$(y(s), \cos\gamma\beta + \sin\gamma e_v^{xf})$$

$$= \frac{(-1)}{2\pi^2} \frac{1}{n} \int_{IBP(x)} w^{xf}(x, s) \frac{ds}{|x - y(s)|} \cdot \sum_{v=1}^{N_v^{xf}} \mu_v^{xf} P_v^{xf}(s, x)$$

$$\frac{(-1)}{2\pi^2} \frac{1}{n} \int_{IBP(x)} w^{xf}(x, s) \frac{ds}{|x - y(s)|} \cdot P^{xf}(s, x),$$

where the superscript xf can be either lf or hf, β is the unit vector pointing from the source position y(s) to the object point x, $D'_f = \partial D_f / \partial s$ are the projection data differentiated with respect to the angular position s of the radiation source, and IBP(x) denotes the back-projection interval of x. The definition of the angle γ can be seen from FIG. 5: a certain object point x is projected onto the point indicated by A on the planar detector 60. For the filtering (i.e. the integration over γ), data along the filter line B have to be combined. Given a point C on this filter line, the angle γ corresponds to the angle between the two rays, which intersect with points A and C.

Moreover, $w^{xf}(x,s)$ is a weighting function, which is subject to the normalization condition $$\sum_{j \in 2Z} (w^{xf}(x, s + j\pi) + w^{xf}(x, s + (j+1)\pi + 2\gamma(x, s))), \tag{8}$$

where γ(x,s) denotes the fan-angle, under which the object point x is seen from source position y(s).

For the low-frequency image $f^{lf}(x)$, the filter lines (corresponding to the vectors $e_v^{lf}$) are chosen such, that $f^{lf}(x)$ contains the contribution of all Radon-planes, which intersect with the helix (in contrast to the back-projection interval) at most n times. The weighting function is constant in the n-PI window:

$$w^{lf}(x,s)=1/n \text{ for } s \in I_{n-pl(x)} \text{ and } 0 \text{ else.} \tag{9}$$

Figure 6:
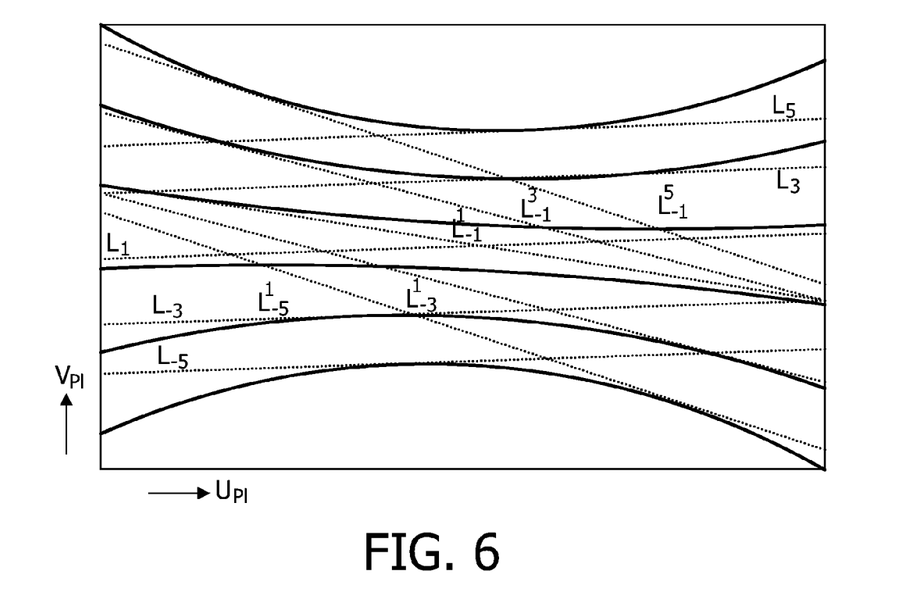
FIG. 6 shows PI-window boundaries and exemplary separation lines on the virtual planar detector area for a 5-PI acquisition.

FIGS. 6 to 10 refer to the definition of different sets of filter lines which correspond to the vectors $e_v^{xf}$ in equation (7). The filter lines can be divided into four groups, namely $ST^{(R)}$, $SL_k^{(R)}$, $SP_k^{(L)}$ and $SP_k^{(R)}$ for $1 \leq k \leq n+1$. The sets $SL_k^{(R)}$ are identical to those known from literature (cf. C. Bontus, T. Koehler, R. Proksa, above). FIG. 6 shows separation lines $L_{-p}^k$ used to define the sets $SL_k^{(R)}$. FIGS. 7-10 show examples of sets $ST^{(R)}$, $SL_k^{(R)}$, $SP_k^{(L)}$, and $SP_k^{(R)}$ on the planar detector. For sets $SL_k^{(R)}$, $SP_k^{(R)}$, and $ST^{(R)}$, the filtering should be performed from left to right, while for sets $SP_k^{(L)}$, the filtering should be performed from right to left. The solid curves in FIGS. 6-10 are the boundaries of different k-PI windows. The straight solid lines in FIGS. 9 and 10 separate different regions. In these different regions, the filter lines are tangential on different k-Pi window boundaries.

Figure 7:
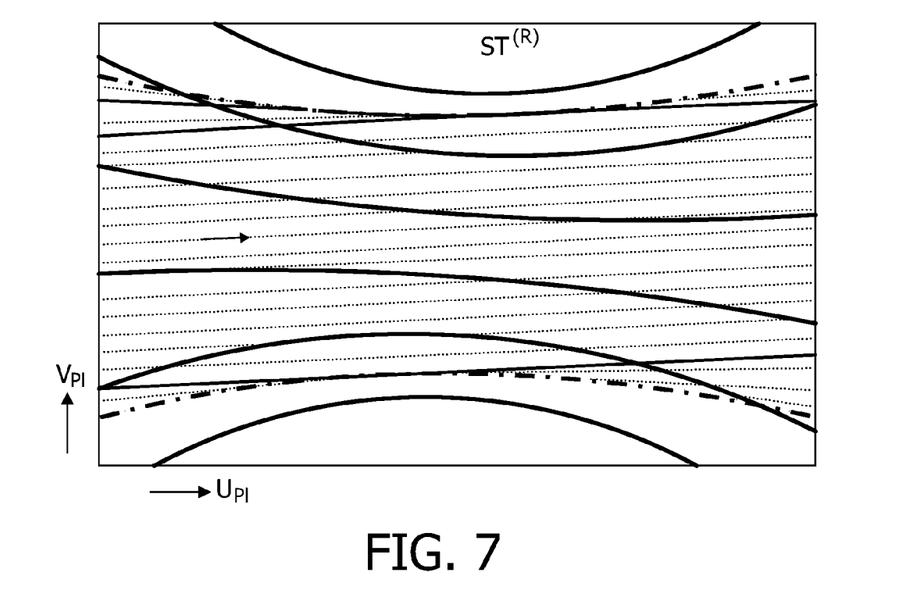
FIG. 7 shows exemplary filter lines of the set $ST^{(R)}$.
Figure 8:
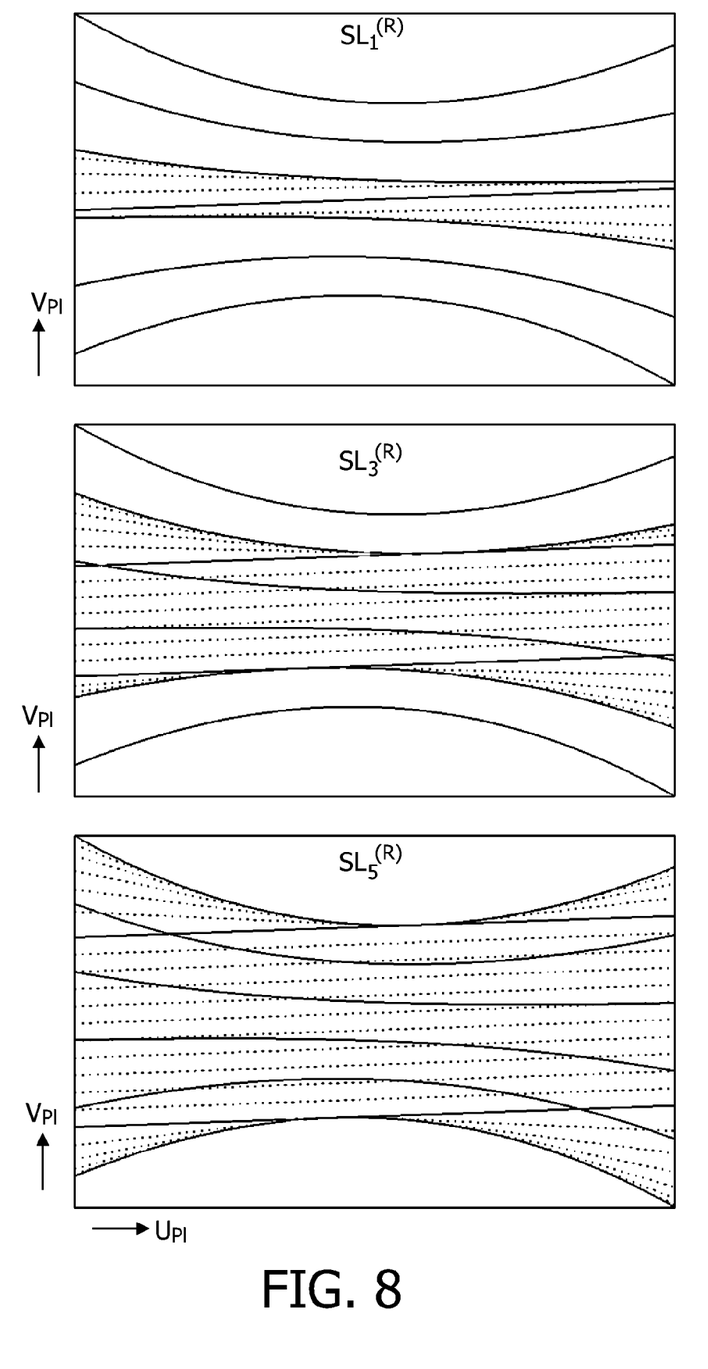
FIG. 8 shows, from top to bottom, exemplary filter lines of the sets $SL_2^{(R)}$, $SL_3^{(R)}$, and $SL_5^{(R)}$.
Figure 9:
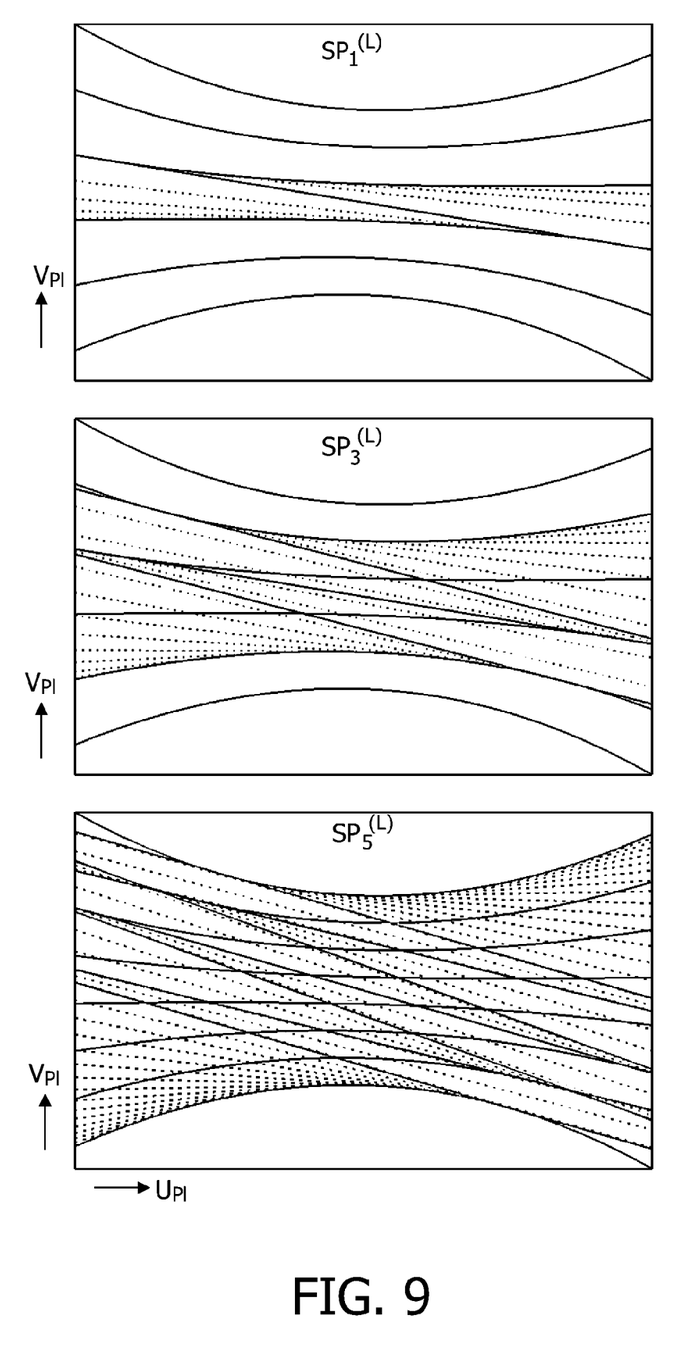
FIG. 9 shows, from top to bottom, exemplary filter lines of the sets $SP_1^{(R)}$, $SP_3^{(R)}$, and $SP_5^{(L)}$.
Figure 10:
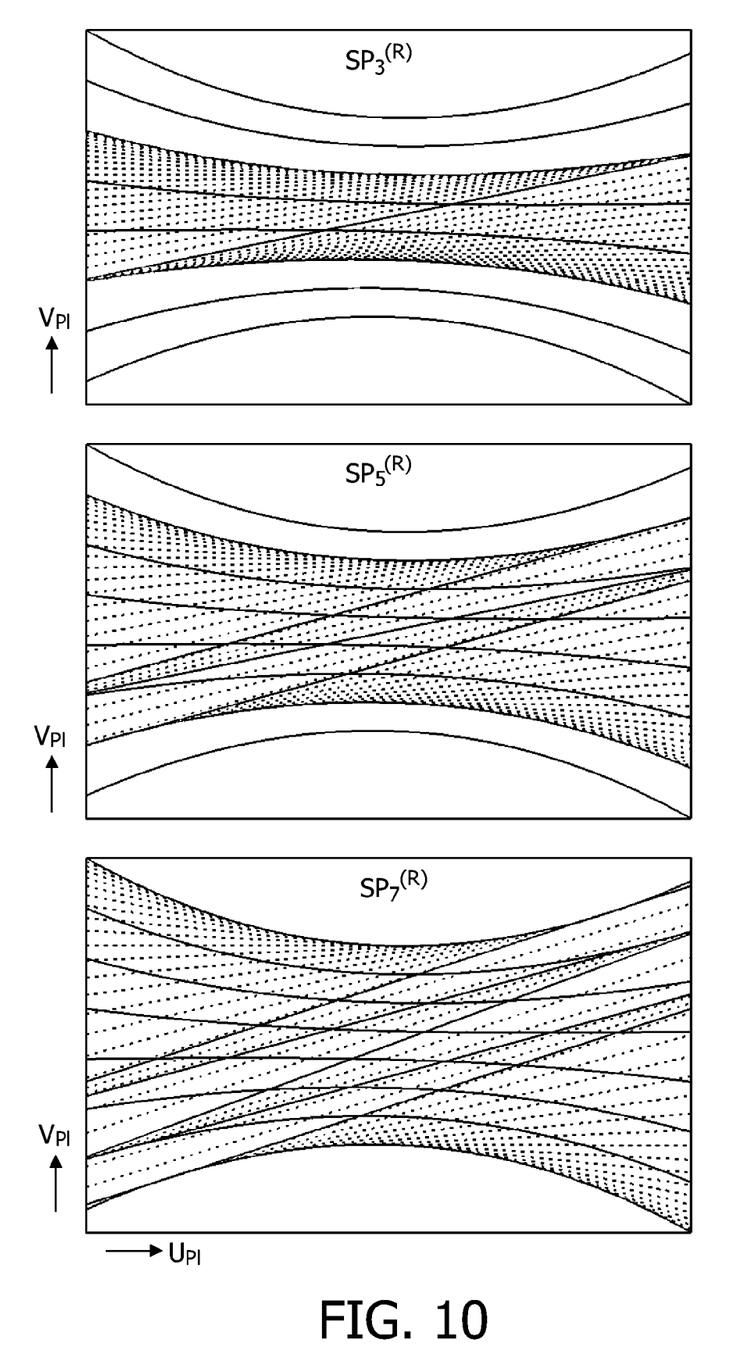
FIG. 10 shows, from top to bottom, exemplary filter lines of the sets $SP_3^{(R)}$, $SP_5^{(R)}$, and $SP_7^{(R)}$.

The dash-dotted lines in FIG. 7 are the projections of the focus-detector boundaries onto the planar-detector. The filter-lines in this Figure, $ST^{(R)}$, are either tangential on these boundaries or parallel to dy(s)/ds, the asymptote on the PI-window. The filter lines $ST^{(R)}$ are introduced in order to be able to use all measured data.

Using the filter lines of FIGS. 7 to 10, the next step of the procedure according to FIG. 2 consists of the generation of two filtered data sets $\Sigma_{\leq n}$, $\Sigma_{>n}$. $\Sigma_{>n}$ contains the contributions of filter line sets $SL_n^{(R)}$, $ST^{(R)}$, $SP_n^{(R)}$, and $SP_n^{(L)}$, with weights (factors $\mu_v^{hf}$ in equation (7)) $-1$, $1$, $½$, and $-½$, respectively.

For $\Sigma_{\leq n}$, the contributions of filter line sets $SL_1^{(R)}$, $SL_3^{(R)}$, ... $SL_n^{(R)}$, $SP_1^{(L)}$, $SP_3^{(L)}$, ... $SP_n^{(L)}$, $SP_3^{(R)}$, $SP_5^{(R)}$, ... $SP_n^{(R)}$ are summed up. The corresponding weights are as follows. Sets $SL_1^{(R)}$ and $SP_1^{(L)}$ get the weight n/3, set $SL_{n\,hu\,(R)}$ gets the weight 1, and for $1<k<n$ set $SL_k^{(R)}$ gets the weight $2n/(k(k+2))$. Set $SP_n^{(R)}$ gets the weight $-½$, and for $1<k<n$ set $SP_n^{(R)}$ gets the weight $-n/(k(k+2))$. Set $SP_n^{(L)}$ gets the weight $½$, and for $1<k<n$ set $SP_k^{(L)}$ gets the weight $n/(k(k+2))$.

It can be shown that $\Sigma_{\leq n}$ contains contributions of Radon-planes with n or less intersection points with the helix (i.e. not with the back-projection interval), while $\Sigma_{>n}$ contains contributions of Radon-planes with more than n intersection points. Moreover, the Radon-planes, which contribute to $\Sigma_{\leq n}$, are weighted uniformly.

From the above definitions it follows that, for the high-frequency image $f^{hf}(x)$, the filter lines are chosen such that almost all Radon-planes, which intersect with the helix more than n times, are weighted equally with 1 (since the filter lines in $ST^{(R)}$ become tangential to the detector boundary, this is not true for all planes), while Radon-planes with at most n intersections receive a weight of 0.

Considering the weighting function $w^{hf}(x,s)$, a detailed analysis shows that a separate treatment of so-called n-PI partners (i.e. projections which are an integer multiple of 180° apart from each other as seen from the object point x) is required. This leads to a normalization of sets of n-PI partners to a weight of 1/n each:

$$\sum_{j \in 2\mathbb{Z}} \left( \begin{array}{c} w^{hf}(x, s + (jn+q)\pi) + \\ w^{hf}(x, s + ((j+1)n + q)\pi + 2\gamma(x,s)) \end{array} \right) = \frac{1}{n} \quad (10)$$

with $q=0, \ldots n-1$. This completes the definition of all components in equation (7).

If images of the cardiac system are reconstructed, the cyclic motion of the object due to heart beat has to be taken into account. This is typically achieved by so-called cardiac gating, i.e. the selected use of measuring values (projections) that were generated during a given window of the heart cycle. The heart phase is typically determined by a simultaneous acquisition of electrocardiographic signals. As was explained above, Radon-planes can be classified into sets of "k-planes" according to the number k of intersections with the source trajectory. Obviously, for a 1-plane, there is no redundancy, such that the corresponding information is lost, if this plane receives a cardiac gating weight of zero. Fortunately, according to the Fourier-slice theorem, these planes contribute only to low-frequency contents, such that a gating is not really necessary. The filter lines defined above separate the data into two parts. The first part contains contributions of Radon-planes, which intersect with the helix (i.e. not with the back-projection interval) n times or less. The second part contains contributions of Radon-planes with more than n intersection points. Cardiac gating is applied only to the second kind of contributions.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A computed tomography reconstruction method, comprising:
    determining an absorption function of object points in an examination zone with a reconstruction computer using two non-empty sets of filtered projections, wherein for a predetermined odd number m≦a second predetermined odd number n:
        a first set of filtered projections yields, when back-projected, a first absorption function that contains only contributions of Radon-planes with at most m intersections with the source trajectory;
        a second set of filtered projections yields, when back-projected, a second absorption function that contains only contributions of Radon-planes with more than m intersections with the source trajectory; and
        at least one of the sets of filtered projections contains contributions from measuring values outside a n-PI window; and
    determining a partial derivative of measuring values with respect to an angular position of a radiation source, the measuring values being generated by parallel rays emanating from different radiation source positions;
    the first and the second set of filtered projections include, for each measuring value, a first and a second filtered value, respectively, wherein:
        each first and second filtered value corresponds to a weighted sum, with filter factors, of first and second intermediate filtered values, respectively, and
        each of said intermediate filtered values is the result of filtering the derived measuring values along an associated filtering line with a K-filter; and
    the absorption function of object points in the examination zone is reconstructed by weighted back-projection of the first and second filtered values.

2. The method according to claim 1, wherein the predetermined odd number m is equal to n.

3. The method according to claim 1, wherein the second set of filtered projections yields, when back-projected, and absorption function that contains contributions from almost all Radon-planes with more than m intersections with the source trajectory.

4. The method according to claim 1, wherein the first and second absorption function are reconstructed from the first and the second set of filtered projections, respectively, and then superposed to yield the final absorption function of object points in the examination zone.

5. The method according to claim 1, wherein the absorption function of object points in the examination zone is reconstructed based on a third set of filtered projections that corresponds to the point-by-point sum of the first and the second set of filtered projections.

6. The method according to claim 1, wherein the first and second intermediate filtered values are generated by integrating the derived measuring values along the associated filter line while applying a K-filter factor of $(1/\sin \gamma)$, wherein $\gamma$ is the angle between a currently considered point and a reference point on the filter line as seen from the source position.

7. The method according to claim 1, wherein m=n and that the first intermediate filtered values are based on one filter line from each of a plurality of sets of filter lines.

8. The method according to claim 1, wherein m=n and that the second intermediate filtered values are based on one filter line from each of a plurality of sets of filter lines with weights $-1, 1, \frac{1}{2}$, and $-\frac{1}{2}$.

9. The method according to claim 1, wherein the weighted back-projection of the first filtered values is done with a weight proportional to $w^{lf}(x,s)/|x-y(s)|$ with $$w^{lf}(x, s) = \begin{cases} 1/n & \text{for } s \in I_{n-PI(x)} \\ 0 & \text{else} \end{cases}$$

wherein
x is the considered object point,
s is the angular position of the radiation source,
y(s) is the spatial position of the radiation source, and
$I_{n-PI(x)}$ is the back-projection interval of x for an n-PI acquisition.

10. The method according to claim 1, wherein the weighted back-projection of the second filtered values is done with a weight proportional to $w^{hf}(x,s)/|x-y(s)|$ with $w^{hf}(x,s)$ obeying the normalization condition $$\sum_{j \in 2Z} \left( \begin{array}{c} w^{hf}(x, s+(jn+q)\pi) + \\ w^{hf}(x, s+((j+1)n+q)\pi + 2\gamma(x,s)) \end{array} \right) = \frac{1}{n}$$

wherein
q=0, ... n−1,
2 Z={ ... −2, 0, 2, 4, ... }
x is the considered object point,
s is the angular position of the radiation source,
y(s) is the spatial position of the radiation source, and
$\gamma(x,s)$ is the fan-angle, under which x is seen from y(s).

11. The method according to claim 1, wherein the elements of one of the sets of filtered projections are selected according to a cardiac gating scheme.

12. A computer tomograph, comprising:
a radiation source for generating a radiation beam which traverses an examination zone or an object present therein,
a drive arrangement which serves to displace an object present in the examination zone and the radiation source relative to one another about an axis of rotation and/or parallel to the axis of rotation,
a detector unit which is coupled to the radiation source and comprises a detector area for the acquisition of measuring values,
a reconstruction unit for reconstructing the spatial distribution of the absorption of an object within the examination zone from the measuring values acquired by the detector unit,
a control unit for controlling the radiation source, the detector unit, the drive arrangement and the reconstruction unit in conformity with the following steps:
determining an absorption function of object points in an examination zone with a reconstruction computer using two non-empty sets of filtered projections, wherein for a predetermined odd number m≦a second predetermined odd number n:
the first set of filtered projections yields, when back-projected, a first absorption function that contains only contributions of Radon-planes with at most m intersections with the source trajectory;
the second set of filtered projections yields, when back-projected, a second absorption function that contains only contributions of Radon-planes with more than m intersections with the source trajectory; and
at least one of the sets of filtered projections contains contributions from measuring values outside a n-PI window; and
determining a partial derivative of measuring values with respect to an angular position of a radiation source, the measuring values being generated by parallel rays emanating from different radiation source positions;
the first and the second set of filtered projections include, for each measuring value, a first and a second filtered value, respectively, wherein:
each first and second filtered value corresponds to a weighted sum, with filter factors, of first and second intermediate filtered values, respectively, and
each of said intermediate filtered values is the result of filtering the derived measuring values along an associated filtering line with a K-filter; and the absorption function of object points in the examination zone is reconstructed by weighted back-projection of the first and second filtered values.

13. The computer tomograph according to claim 12, wherein the predetermined odd number m is equal to n.

14. The computer tomograph according to claim 12, wherein the second set of filtered projections yields, when back-projected, and absorption function that contains contributions from almost all Radon-planes with more than m intersections with the source trajectory.

15. The computer tomograph according to claim 12, wherein the first and second absorption function are reconstructed from the first and the second set of filtered projections, respectively, and then superposed to yield the final absorption function of object points in the examination zone.

16. The computer tomograph according to claim 12, wherein the absorption function of object points in the examination zone is reconstructed based on a third set of filtered projections that corresponds to the point-by-point sum of the first and the second set of filtered projections.

17. A non-transitory computer-readable medium containing instructions for a control unit for controlling a radiation source, a detector unit, a drive arrangement and a reconstruction unit of a computer tomograph so as to execute the steps of:

determining an absorption function of object points in an examination zone with a reconstruction computer using two non-empty sets of filtered projections, wherein for a predetermined odd number $m \leq$ a second predetermined odd number n:

the first set of filtered projections yields, when back-projected, a first absorption function that contains only contributions of Radon-planes with at most m intersections with the source trajectory;

the second set of filtered projections yields, when back-projected, a second absorption function that contains only contributions of Radon-planes with more than m intersections with the source trajectory; and at least one of the sets of filtered projections contains contributions from measuring values outside the n-PI window; and determining a partial derivative of measuring values with respect to an angular position of a radiation source, the measuring values being generated by parallel rays emanating from different radiation source positions;

the first and the second set of filtered projections include, for each measuring value, a first and a second filtered value, respectively, wherein:

each first and second filtered value corresponds to a weighted sum, with filter factors, of first and second intermediate filtered values, respectively, and each of said intermediate filtered values is the result of filtering the derived measuring values along an associated filtering line with a K-filter; and the absorption function of object points in the examination zone is reconstructed by weighted back-projection of the first and second filtered values.

* * * * *